Figure 1:
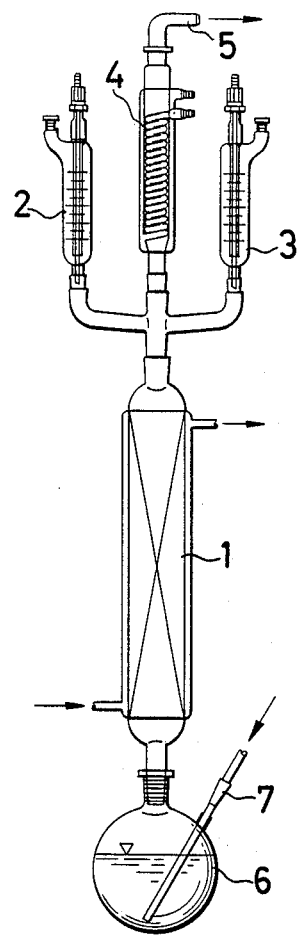

United States Patent [19]

Wellbrock et al.

[11] Patent Number: 4,803,015
[45] Date of Patent: Feb. 7, 1989

[54] CONTINUOUS PROCESS FOR THE PRODUCTION OF ACYLOXYBENZENESULFONIC ACIDS

[75] Inventors: Werner Wellbrock, Bad Soden am Taunus; Adolf Studeneer, Kelkheim, both of Fed. Rep. of Germany

[73] Assignee: Hoechst Aktiengesellschaft, Fed. Rep. of Germany

[21] Appl. No.: 922,275

[22] Filed: Oct. 23, 1986

[30] Foreign Application Priority Data

Oct. 26, 1985 [DE] Fed. Rep. of Germany ....... 3538141

[51] Int. Cl.$^4$ ........................................... C07C 143/90
[52] U.S. Cl. ..................................................... 260/402
[58] Field of Search .......................................... 260/402

[56] References Cited

U.S. PATENT DOCUMENTS 3,394,155  7/1968  Cahn et al. ........................... 260/400
3,503,888  3/1970  Miller et al. ......................... 252/117

FOREIGN PATENT DOCUMENTS 0098021  1/1984  European Pat. Off. .
0105672  4/1984  European Pat. Off. .
0105673  4/1984  European Pat. Off. .
0125641  11/1984  European Pat. Off. .
2559768  10/1985  France .
2559769  10/1985  France .

*Primary Examiner*—Anton H. Sutto
*Attorney, Agent, or Firm*—Connolly and Hutz

[57] ABSTRACT

A process for the continuous production of $C_7$–$Cl_2$-acyloxybenzenesulfonic acids, wherein phenol and a sulfonating reagent, diluted with an aliphatic $C_7$–$Cl_2$-carboxylic acid, is charged to the top of a continuous-flow reactor heated to 80°–100° and the mixture of phenolsulfonic acid and the aliphatic carboxylic acid, leaving the bottom end of this continuous-flow reactor, and a chlorinating reagent are charged to the top of a second continuous-flow reactor, nitrogen being passed in counter-current through both continuous-flow reactors.

2 Claims, 1 Drawing Sheet

U.S. Patent

Feb. 7, 1989

4,803,015

CONTINUOUS PROCESS FOR THE PRODUCTION OF ACYLOXYBENZENESULFONIC ACIDS

Acyloxybenzenesulfonic acids and their salts are compounds, known for a long time, which have surfactant-like properties and which, in addition, can be used as perborate activators, according to EP-A No. 98/021. A number of processes for the production of these compounds are known (FR-A No. 2,559,768, FR-A No. 2,559,769, EP-A No. 105,672, EP-A No. 105,673, EP-A No. 125,641, U.S. Pat. No. 3,394,155 and U.S. Pat. No. 3,503,888). However, these processes do not run continuously. It was therefore the object to develop a continuously operating process suitable for the large-scale industrial production of such acyloxybenzenesulfonic acids, in particular for the production of isononanoylbenzenesulfonic acid.

The invention relates to a process for the continuous production of $C_7$–$C_{12}$-acyloxybenzenesulfonic acids, which comprises charging phenol and a sulfonating reagent, diluted with an aliphatic $C_7$–$C_{12}$-carboxylic acid, to the top of a continuous-flow reactor heated to 80°–100° C. and charging the mixture of phenolsulfonic acid and the aliphatic carboxylic acid leaving the bottom end of this continuous-flow reactor, and a chlorinating reagent to the top of a second continuous-flow reactor, nitrogen being passed in counter-current through both continuous-flow reactors.

Preferably, isononanoyloxybenzenesulfonic acid is produced by this process.

Figure 2:
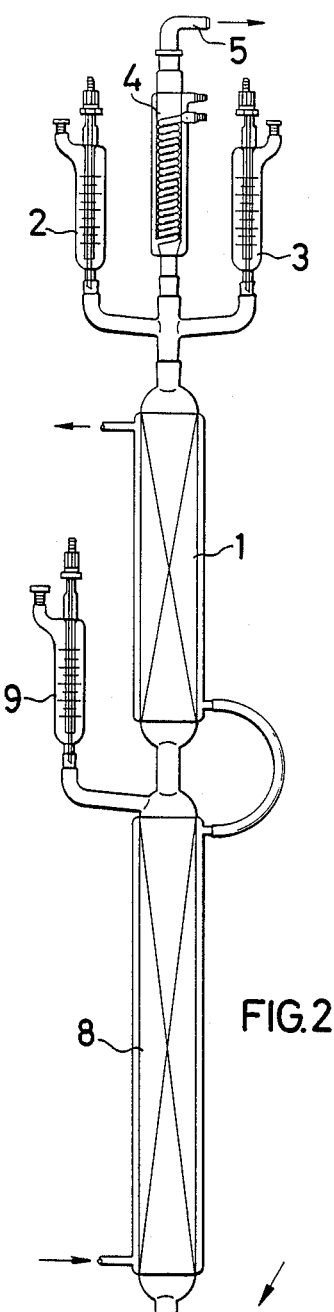

Equipment suitable for producing this product is shown in FIGS. 1 and 2.

In a first stage (FIG. 1), phenol is first sulfonated in a continuousflow reactor 1 by means of a sulfonating reagent, for example sulfuric acid or oleum, preferably chlorosulfonic acid. Both starting compounds are charged from two graduated funnels 2 and 3 to the continuous-flow reactor, which in addition is also provided with a reflux condenser 4 and a gas discharge tube 5. Advantageously, both starting compounds are diluted with isononanoic acid, in particular in such a ratio that there are approximately the same volumes in both graduated funnels. The total quantity of isononanoic acid corresponds approximately to the theoretical quantity of this acid which is required for esterifying the phenolsulfonic acid in the second stage. The continuous-flow reactor in this first stage is heated to a temperature to 80° to 100° C., preferably 95° C. The phenolsulfonic acid thus produced, dissolved in isononanoic acid, is collected in a receiver 6 at the bottom end of the continuous-flow reactor. A steady inert gas stream is passed through the continuous-flow reactor. The inlet 7 for this inert gas is located such that the inert gas also bubbles through the phenolsulfonic acid in the receiver.

For esterification, this phenolsulfonic acid dissolved in isononanoic acid is charged via a graduated funnel to the top of a second continuous-flow reactor. However, the intermediate isolation of the phenolsulfonic acid, as shown in FIG. 1, can also be omitted, using the equipment according to FIG. 2. In this case, the first continuous-flow reactor is directly connected to the second continuous-flow reactor 8, and the mixture of phenylsulfonic acid and isononanoic acid is transferred directly into the second continuous-flow reactor. For the esterification taking place in the latter, a chlorination reagent, preferably thionyl chloride, is also required and this is added from a further graduated funnel 9 to the second continuous-flow reactor. The quantity of thionyl chloride per mole of phenylsulfonic acid is 1 mole, but an excess of up to 10% is also possible. The temperature in this continuous-flow reactor should be 45° to 65° C., preferably 55° C.

Example

In the equipment according to FIG. 1, a mixture of 178.8 g (1.53 mole) of chlorosulfonic acid and 136.5 g (0.86 mole) of isononanoic acid was placed into one of the two graduated funnels and a mixture of 143 g (1.52 mole) of phenol and 104 g (0.66 mole) of isononanoic acid was placed into the other, and the two mixtures were added under control to the continuous-flow reactor in such a way that the residence time was about 7 minutes. The total time for adding the starting compounds to the reactor under control was about 2 hours. The reactor, heated to 95° C. under thermostatic control, had a length of 60 cm and was packed with glass rings. Throughout the reaction period, 10 liters of nitrogen per hour were passed through the receiver and through the reactor. This gave a 93.3% yield of crude phenolsulfonic acid diluted with isononanoic acid, of the following composition:

39.7% of 4-phenolsulfonic acid,
10.9% of 2-phenolsulfonic acid, less than 0.05% of hydroxybenzene-2,4-disulfonic acid and
1.8% of phenol.

For esterification, this mixture of crude phenolsulfonic acid with isononanoic acid was placed into a graduated funnel of equipment of the same type as shown in FIG. 1. 110.1 g of thionyl chloride were placed into the second graduated funnel. The two components were then charged to the reactor in such a way that the residence time was about 50 minutes. The time taken for adding the reaction components under control to the reactor was about 170 minutes. The reactor had a length of 220 cm, was packed with glass rings of 6 mm diameter and was heated to a temperature of 55° C. 10 liters per hour of nitrogen were conducted through the receiver for collecting the isononanoyloxybenzenesulfonic acid formed and accordingly also through the continuous-flow reactor. This gave 270 g of isononanoyloxybenzenesulfonic acid of the following composition:

63.9% of 4-isononanoyloxybenzenesulfonic acid,
11.5% of 2-isononanoyloxybenzenesulfonic acid,
2.4% of 4-phenolsulfonic acid,
1.2% of 2-phenolsulfonic acid and
1.6% of hydroxybenzene-2,4-disulfonic acid.

We claim:

1. A process for the continuous production of $C_7$–$C_{12}$-acyloxybenzenesulfonic acids, which comprises charging phenol and a sulfonating agent, diluted with an aliphatic $C_7$–$C_{12}$-carboxylic acid, to the top of a continuous-flow reactor heated to 80°–100° C. and charging the mixture of phenolsulfonic acid and the aliphatic carboxylic acid leaving the bottom end of this con- tinuous-flow reactor, and a chlorinating agent to the top of a second continuous-flow reactor heated to 45°–65° C., nitrogen being passed in counter-currnnt through both continuous-flow reactors.

2. The process as claimed in claim 1, wherein isononanoyloxybenzenesulfonic acid is produced.

* * * * *